(12) United States Patent
Gañan-Cálvo (10) Patent No.: US 6,386,463 B1
(45) Date of Patent: May 14, 2002

(54) FUEL INJECTION NOZZLE AND METHOD OF USE

(75) Inventor: Alfonso Gañan-Cálvo, Seville (ES)

(73) Assignee: Universidad de Sevilla, Seville (ES)

( * ) Notice: Subject to any disclaimer, the term of this patent is extended or adjusted under 35 U.S.C. 154(b) by 0 days.

(21) Appl. No.: 09/604,935

(22) Filed: Jun. 27, 2000

Related U.S. Application Data (63) Continuation of application No. 09/191,787, filed on Nov. 13, 1998, which is a continuation of application No. 09/192,091, filed on Nov. 13, 1998, which is a continuation-in-part of application No. 09/171,518, filed as application No. PCT/ES97/00034 on Feb. 18, 1997.

(30) Foreign Application Priority Data

May 13, 1996 (ES) ............................................. 9601101
Dec. 17, 1997 (ES) ............................................. 9702654

(51) Int. Cl.[7] .............................................. A62C 5/02
(52) U.S. Cl. ........................... 239/8; 239/424; 239/418; 239/338; 123/585; 222/420; 261/78.1; 73/864.81
(58) Field of Search ........................ 239/5, 8, 86, 417, 239/418, 423, 424, 424.5, 425, 291, 338, 433; 123/531, 585; 261/78.1, 116; 222/420; 73/864.81

(56) References Cited

U.S. PATENT DOCUMENTS

| 2,714,833 A | * | 8/1955 | Gilbert, Jr. ................... 239/424 |
| 3,700,170 A | | 10/1972 | Blanka et al. |
| 3,804,255 A | | 4/1974 | Speece |

(List continued on next page.)

FOREIGN PATENT DOCUMENTS

| CH | 563807 | 7/1975 |
| DE | 4031262 A1 | 4/1992 |
| EP | 0 249 186 A1 | 12/1987 |
| EP | 0 250 164 A2 | 12/1987 |
| GB | 2255291 A | 11/1992 |
| GB | 2099078 A | 12/1992 |
| JP | 59174561 A | 10/1984 |
| JP | 03169331 | 7/1991 |
| WO | WO 90/05583 | 5/1990 |
| WO | WO 91/18682 | 12/1991 |
| WO | WO 94/11116 | 5/1994 |
| WO | WO 94/23129 | 10/1994 |
| WO | WO 95/23030 | 8/1995 |
| WO | WO 96/16326 | 5/1996 |
| WO | WO 97/43048 | 11/1997 |
| WO | WO 97/44080 | 11/1997 |

OTHER PUBLICATIONS

Bowden et al., Science 276:233–5 (1997).
Brenn et al., *Chemical Engineering Science,* 52(2):237–244 (Jan. 1997) (Abstract).
Borchardt et al., *Chemistry & Biology,* 4(12):961–968 (1997).
Chin et al., *Trans. ASME J. Eng. Gas Turbines Power,* 106:639–644 (1983).
Cloupeau et al. (1989), *J. Electrostat* 22:135–159.

(List continued on next page.)

Primary Examiner—David A. Scherbel
Assistant Examiner—Dina Q. Nguyen
(74) Attorney, Agent, or Firm—Karl Bozicevic; Bozicevic, Field & Francis LLP (57) ABSTRACT

Atomized particles within a desired size range (e.g., 1 micron to about 5 microns) are produced from two immiscible fluids, the first a fuel source containing the formulation to be atomized, and a second fluid source which is contained in a pressure chamber surrounding at least the area where the first liquid is to be provided. The invention provides a method for the formation of small, relatively uniform fuel particles for use in internal combustion engines and a nozzle-type apparatus for providing the particles to a combustion chamber.

11 Claims, 6 Drawing Sheets

U.S. PATENT DOCUMENTS

| | | | |
|---|---|---|---|
| 4,017,253 A | * | 4/1977 | Wielang et al. ............. 239/424 |
| 4,141,055 A | | 2/1979 | Berry et al. |
| 4,162,282 A | | 7/1979 | Fulwyler et al. |
| 4,347,935 A | | 9/1982 | Merrill |
| 4,352,789 A | | 10/1982 | Thiel |
| 4,363,446 A | | 12/1982 | Jaeggle et al. |
| 4,444,961 A | | 4/1984 | Timm |
| 4,462,543 A | * | 7/1984 | Yam .......................... 239/424 |
| 4,603,671 A | | 8/1986 | Yoshinaga et al. |
| 4,617,898 A | | 10/1986 | Gayler |
| 4,627,812 A | * | 12/1986 | Kelly et al. |
| 4,628,040 A | | 12/1986 | Green et al. |
| 4,662,338 A | | 5/1987 | Itoh et al. |
| 4,677,958 A | * | 7/1987 | Gayler ........................ 123/585 |
| 4,681,071 A | * | 7/1987 | Smith ......................... 123/585 |
| 4,717,049 A | | 1/1988 | Green et al. |
| 4,738,614 A | * | 4/1988 | Snyder et al. .............. 239/433 |
| 4,752,303 A | * | 6/1988 | Materne ..................... 239/417 |
| 4,781,968 A | | 11/1988 | Kellerman |
| 4,797,087 A | * | 1/1989 | Gitman ....................... 239/423 |
| 4,865,444 A | * | 9/1989 | Green et al. |
| 4,917,857 A | | 4/1990 | Jaeckel |
| 5,020,498 A | | 6/1991 | Linder et al. |
| 5,077,176 A | | 12/1991 | Baggio et al. |
| 5,087,292 A | | 2/1992 | Garrido |
| 5,174,247 A | | 12/1992 | Tosa et al. |
| 5,180,465 A | | 1/1993 | Seki et al. |
| 5,194,915 A | | 3/1993 | Gilby |
| 5,230,850 A | | 7/1993 | Lewis |
| 5,364,632 A | | 11/1994 | Benita et al. |
| 5,364,838 A | | 11/1994 | Rubsamen |
| 5,372,867 A | | 12/1994 | Hasegawa et al. |
| 5,397,001 A | | 3/1995 | Yoon et al. |
| 5,404,871 A | | 4/1995 | Goodman et al. |
| 5,458,292 A | | 10/1995 | Hapeman |
| 5,522,385 A | | 6/1996 | Lloyd et al. |
| 5,554,646 A | | 9/1996 | Cook et al. |
| 5,597,491 A | | 1/1997 | Winkler |
| 5,617,997 A | * | 4/1997 | Kobayashi et al. ............ 239/8 |
| 5,697,341 A | | 12/1997 | Ausman et al. |
| 5,740,794 A | | 4/1998 | Smith et al. |
| 5,775,320 A | | 7/1998 | Patton et al. |
| 6,142,765 A | * | 11/2000 | Ramaseder et al. ...... 239/424.5 |

OTHER PUBLICATIONS

Fernández de la Mora et al. (1994), *J. Fluid Mech.* 260:155–184.

Forbes et al., *J. Austral. Math. Soc. Ser. B.*, 32:231–249 (1990).

Gañán–Calvo et al. (1997), *J. Aerosol Sci.* 28:249–275.

Gauthier, *Optics & Laser Technology,* 29(7): 389–399 (Oct. 1997).

Hartman et al. (1997), "Electrohydrodynamic Atomization in the Cone–Jet Mode," Paper presented at the ESF Workshop on Electrospray, Sevilla, Feb. 28–Mar. 1, 1997 [see also the papers contained in the Special Issue for Electrosprays (1994)].

Huck et al., *Journal of American Chemical Society* pp. 8267–8268 (1998).

Jasuja, *ASME Paper* 82–GT–32 (1982).

Liu et al. (1974), *J. Coloid Interface Sci.* 47:155–171.

Lorenzetto et al., *AIAA J.*, 15:1006–1010 (1977).

Nukiyama et al., *Trans. Soc. Mech. Eng. Jpn.,* 5:68–75 (1939).

Lord Rayleigh (1879), *Proc. London Math. Soc. 10*:4–13.

Service et al., (1997), *Science,* 277:1199–1200.

Singler et al., *Phys. Fluids A,* 5:1156–1166 (1993).

Tuck et al., *J. Austral. Math. Soc. Ser. B.,* 25:433–450 (1984).

Ünal, *Metall. Trans. B.,* 20B:613–622 (1989).

Whitesides et al., *Science* 254:1312–9 (1991).

Wigg, *J. Inst. Fuel,* 27:500–505 (1964).

Winfree et al., *Nature,* 394539–44 (1998).

* cited by examiner

FUEL INJECTION NOZZLE AND METHOD OF USE

CROSS REFERENCES

This application is a continuation of earlier filed application Ser. No. 09/191,787 filed Nov. 13, 1998 which is a continuation to U.S. application Ser. No. 09/192,091, filed Nov. 13, 1998; which is a c-i-p to U.S. application Ser. No. 09/171,518, filed Oct. 20, 1998; which is a 371 to PCT application Ser. No. PCT/ES97/00034, filed Feb. 18, 1997; and claims priority to Spanish Applications P9601101, filed May 13, 1996 and P9702654, filed Dec 17, 1997.

FIELD OF THE INVENTION

This invention relates generally to a fuel injection apparatus, and specifically to fuel injection nozzles for use in an internal combustion engine.

BACKGROUND OF THE INVENTION

A number of different types of fuel injectors are known in the art, and these devices generally use conventional fuel injection nozzles to introduce droplets of fuel into the combustion chamber of an engine, thus increasing the surface area of fuel available for reaction. Increasing the surface area of the fuel affords a more efficient combustion reaction in internal combustion engines.

A number of improvements have been made to the fuel injection process in internal combustion engines that allow such fuel injection devices to function more efficiently within the fuel injection system. For example, U.S. Pat. No. 5,020,498 describes a fuel injection apparatus designed to provide a direct connection to supply lines or pressure lines to avoid pressure waves that may arise in the supply line network, which can have a disruptive effect on the injection quantity. In this device, a direct line connection with fuel supply lines is avoided during the injection event, the result being that pressure waves that develop in the lines cannot affect the injection event. In another example, British patent No. 2,099,078A describes the use of a compound rotary valve to control the timing and duration of opening the intensifier cavity to either the high pressure actuation fluid or to the low pressure fuel drain. In a further example, U.S. Pat. No. 5,697,341 describes fuel injectors that are hydraulically actuated, with fuel pressurized by a plunger driven by an intensifier piston. Fuel in the hydraulically actuated devices can be metered into the injector either by biasing the plunger with a return spring, or by pressurizing the fuel to hydraulically push the plunger in a retracting direction between injection events.

Although the quantity and quality of injection in the fuel injection apparatus have been improved by altering the method and route of fuel delivery to the device, these improvements have not addressed the efficiency limitations of the nozzle mechanism per se. Each of the above-described systems, which have enhanced delivery of fuel, use a conventional VOP type of needle check and nozzle. Examples of conventional nozzles can be found in: U.S. Pat. Nos. 4,662,338; 4,603,671; and 4,363,446. Such methods of delivery through conventional nozzles have technological limitations, such as limits on the minimum size of the expelled fuel droplets, the amount of energy transfer necessary to produce the fuel droplets, and clogging of the nozzle due to build up of residue left by the fuel composition.

There is a need in the art for a method of more efficient injection of fuel into an internal combustion engine or other similar device, e.g. by decreasing the size of the fuel droplet thus increasing the surface area available for the combustion reaction. Accordingly, there is a need in the art for a nozzle to improve the efficiency of fuel delivery in a fuel injection system.

SUMMARY OF THE INVENTION

A fuel injection nozzle for use in a fuel injection apparatus of an internal combustion engine is provided. The fuel injection nozzle of the present invention has a unique fuel delivery system comprised of a pressure chamber and a fuel source. Atomized fuel particles within a desired size range (e.g., 5 micron to about 500 microns, and preferably between 10 and 100 microns) are produced from a liquid fuel formulation provided via a fuel supply opening. The fuel may be provided in any desired manner, e.g., forced through a channel of a feeding needle and expelled out of an exit opening of the needle. Simultaneously, a second fluid contained in a pressure chamber which surrounds at least the area where the formulation is provided, e.g., surrounds the exit opening of the needle, is forced out of an opening positioned in front of the flow path of the provided fuel, e.g. in front of the fuel expelled from the feeding needle. Various parameters are adjusted to obtain a stable fuel-fluid interface and a stable capillary microjet of the fuel, which allows formation of atomized fuel particles on exiting the opening of the pressurized chamber.

Fuel injectors of the invention have three significant advantages over prior injectors. First, fuel never contacts the periphery of the exit orifice from which it is emitted because the fuel stream is surrounded by a gas (e.g. air) which flows into the exit orifice. Thus, clogging of the orifice is eliminated or substantially reduced. Second, the fuel exits the orifice and forms very small particles which are substantially uniform in size, thereby allowing faster and more controlled combustion of the fuel. Third, by using the methods described herein, the amount of energy needed to produce aerosolized particles of fuel is substantially less than that required by other methods.

An object of the invention is to provide a device for efficient delivery of a fuel to a combustion chamber of an internal combustion engine.

Another object is to provide a method of creating an fuel aerosol of consistent particle size, which increases the surface area available for a combustion reaction.

A feature of the invention is that the diameter of the opening from which fluid is expelled, the diameter of the opening from which fluid is expelled and the distance between these two openings is adjustable and is adjusted to obtain a stable fuel-fluid interface which results in a stable capillary microjet being formed by the fuel expelled, which microjet is focused on an exit opening by the flow of surrounding fluid (e.g. air).

An advantage of the invention is that it consistently produces fuel particles within a desired particle diameter range.

Another advantage of the invention is that the method of aerosolization of the fuel discourages agglomeration of the particles upon entering the combustion chamber.

An advantage of the invention is that fuel injection using the device of the invention is energy efficient.

Another advantage is that the structure of the device and its use are simple.

Another advantage is that clogging of the exit opening of the pressure chamber is substantially eliminated because the fuel is kept out of contact with the surface of the exit opening by a surrounding focused funnel of fluid, which flows out of the pressure chamber exit opening.

Yet another advantage is that particles produced are substantially smaller in size than would be expected based on the diameter of the exit opening of the pressure chamber due to focusing the flow of the fuel with the flow of surrounding fluid.

An aspect of the invention is a fuel injection nozzle that is one element of a fuel injection device and system.

Another aspect of the invention is a device which provides for the rapid engagement and disengagement of the aerosolization process.

These and other aspects, objects, features and advantages will become apparent to those skilled in the art upon reading this disclosure in combination with the figures provided.

BRIEF DESCRIPTION OF THE DRAWINGS

FIG. 1A schematic view showing the basic components of one embodiment of the invention with a cylindrical feeding needle as a source of formulation.

FIG. 1B is an enlarged schematic view of the cylindrical feeding needle shown in FIG. 1A.

FIG. 2 is a schematic view of another embodiment of the invention with two concentric tubes in a single feeding needle unit as a source of formulation.

FIG. 3 is a schematic view of yet another embodiment showing a wedge-shaped planar source of formulation.

FIG. 3*a* illustrates a cross-sectional side view of the planar feeding source and the interaction of the fluids.

FIG. 3*b* show a frontal view of the openings in the pressure chamber, with the multiple openings through which the atomizate exits the device.

FIG. 3*c* illustrates the channels that are optionally formed within the planar feeding member. The channels aligned with the openings in the pressure chamber.

FIG. 4 is a schematic view of a stable capillary microjet being formed and flowing through an exit opening to thereafter form a monodisperse aerosol.

FIG. 5 is a graph of data where 350 measured valves of $d_j/d_o$ versus $Q/Q_o$ are plotted.

FIGS. 6*a* and 6*b* are schematic views of an exemplary use of the embodiment of FIGS. 1A and 1B in an injection apparatus.

FIGS. 7*a* and 7*b* are schematic views of an exemplary use of the embodiment of FIG. 3, in which the injection device is comprised of circular feeding elements positioned in multiple, concentric pressure chambers.

DETAILED DESCRIPTION OF PREFERRED EMBODIMENTS

Before the present device and method are described, it is to be understood that this invention is not limited to the particular components and steps described, as such may, of course, vary. It is also to be understood that the terminology used herein is for the purpose of describing particular embodiments only, and is not intended to be limiting, since the scope of the present invention will he limited only by the appended claims.

It must be noted that as used herein and in the appended claims, the singular forms "a", "and," and "the" include plural referents unless the context clearly dictates otherwise. Thus, for example, reference to "a particle" includes a plurality of particles and reference to "a fuel" includes reference to a mixture of fuels, and equivalents thereof known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "particles", "atomized particles" and "atomized particles of formulation" are used interchangeably herein and shall mean particles of formulation that have been atomized using the device and method of the invention.

The terms "formulation" and "fuel formulation", as used herein interchangeably, refer to any matter which is desired to be atomized. The formulation may be any fluid used to initiate and/or participate in a combustion reaction, preferably a solution comprised of hydrocarbon alkanes, e.g. gasoline or kerosene. The formulation is preferably presented in the method of the invention as the first fluid, although it may be presented as the second fluid. Formulations can also be a combination of fuels, either in solution, suspension or an emulsion.

The terms "air", "particle tree air" and the like, are used interchangeably herein to describe a volume of air which is substantially free of other material and, in particular, free of particles intentionally added such as particles of formulation. The term means that the air does not include particles of formulation which have been intentionally added but is not intended to imply that the normal surrounding air has been filtered or treated to remove all particles although filtering can take place. Air may be filtered for use in the invention, or alternatively another gas may be used.

Device in General

The present invention can be applied to the creation of particles for any number of uses. The present disclosure focuses on use of general technology in delivering fuel to internal combustion engines, e.g. volumetric and spark engines. The invention is not to be limited to such uses, however, as related uses of the method and device of the present invention, such as delivery of combustible materials in gas turbines, burners, heaters and the like will be applicable and readily seen by those skilled in the art.

The technology of the invention comprises (1) a means for supplying a first fluid; and (2) a pressure chamber supplied with a second fluid. The first fluid is generally a liquid and preferably a hydrocarbon fuel comprised of alkanes. The second fluid is generally either a gas, preferably air, or a hydrophilic liquid. The critical property of the fluids is that the first and second fluid are sufficiently different from each other so as to allow for the formation of a stable microjet of the first fluid moving from the supply means to an exit port of the pressure chamber. Notwithstanding these different combinations of gas-liquid, liquid-gas, and liquid-liquid the invention is generally described with a liquid formulation being expelled from the supply means and forming a stable microjet due to interaction with surrounding air flow focusing the microjet to flow out of an exit of the pressure chamber.

Formation of the microjet and its acceleration and ultimate particle formation are based on the abrupt pressure drop associated with the steep acceleration experienced by the first fluid (e.g., a liquid) on passing through an exit orifice of the pressure chamber which holds the second fluid. On leaving the chamber the flow undergoes a large pressure difference between the first fluid (e.g., a liquid) and the second fluid (e.g., a gas), which in turn produces a highly curved zone on the first fluid (e.g., liquid) surface near the exit port of the pressure chamber and in the formation of a cuspidal point from which a steady microjet flows provided the amount of the first fluid (e.g., the liquid) withdrawn through the exit port of the pressure chamber is replenished. Thus, in the same way that a glass lens or a lens of the eye focuses light to a given point, the flow of the gas surrounds and focuses the liquid into a stable microjet. The focusing effect of the surrounding flow of gas creates a stream of liquid which is substantially smaller in diameter than the diameter of the exit orifice of the pressure chamber. This allows liquid to flow out of the pressure chamber orifice without touching the orifice, providing advantages including (1) clogging of the exit orifice is virtually eliminated, (2) contamination of flow due to contact with substances (e.g. undesirable particulates) on the orifice opening is virtually eliminated, and (3) the diameter of the stream and the resulting particles are smaller than the diameter of the exit orifice of the chamber. This is particularly desirable because it is difficult to precisely engineer holes which are very small in diameter. Further, in the absence of the focusing effect (and formation a stable microjet) flow of liquid out of an opening will result in particles which have about twice the diameter of the exit opening. An additional advantage is that the particles are not prone to agglomeration following exit from the chamber.

Specific embodiments of aerosol creation devices are now described.

Figures 1A, 1B, 2:
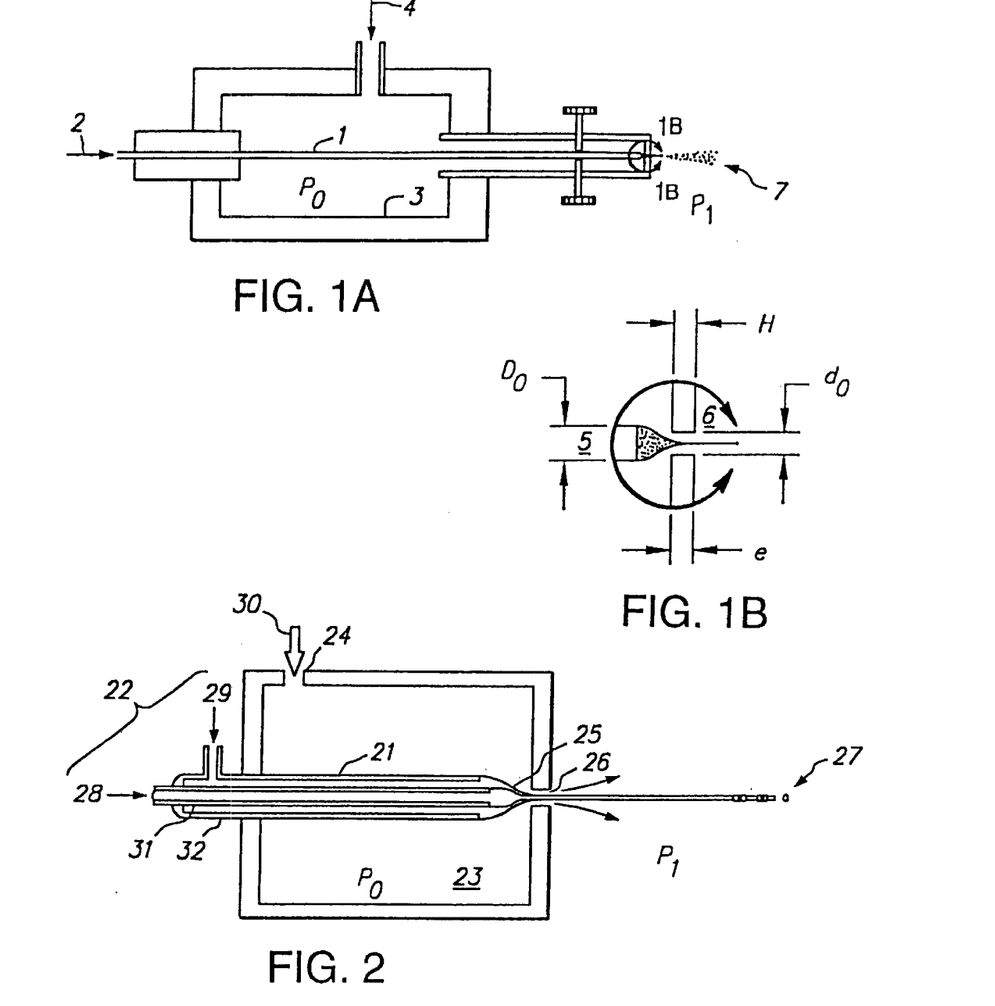

Embodiment of FIG. 1

A first embodiment of the invention where the supply means is a cylindrical feeding needle supplying liquid into a pressurized chamber of gas is described below with reference to FIGS. 1A and 1B.

The components of the embodiment of FIGS. 1A and 1B are as follows:

1. Feeding needle—also referred to generally as a fluid source and a tube.
2. End of the feeding needle used to insert the liquid to be atomized.
3. Pressure chamber.
4. Orifice used as gas inlet.
5. End of the feeding needle used to evacuate the liquid to be atomized.
6. Orifice through which withdrawal takes place.
7. Atomizate (spray)—also referred to as aerosol.

$D_0$=diameter of the feeding needle; $d_0$=diameter of the orifice through which the microjet is passed; e=axial length of the orifice through which withdrawal takes place; H=distance from the feeding needle to the microjet outlet; $P_0$=pressure inside the chamber; $P_a$=atmospheric pressure.

A fuel injection nozzle of the invention may be any size but is preferably sized for use in a conventional fuel injection apparatus. Although the device can be configured in a variety of designs, the different designs will all include the essential components shown in FIGS. 1A and 1B or components which perform an equivalent function and obtain the desired results. Specifically, a fuel injection nozzle of the invention will be comprised of at least one source of formulation (e.g., a feeding needle with an opening 2) into which a liquid flowable formulation can be fed and an exit opening 5 from which the formulation can be expelled. The feeding needle 1, or at least its exit opening 5, is encompassed by a pressure chamber 3. The chamber 3 has inlet opening 4 which is used to feed gas into the chamber 3 and an exit opening 6 through which gas from the pressure chamber and liquid formulation from the feeding needle 3 are expelled creating an aerosol.

In FIGS. 1A and 1B, the feeding needle and pressure chamber are configured to obtain a desired result of producing an aerosol wherein the particles are small and uniform in size. Preferably the particles have a size which is in a range of 0.5 to 500 microns, more preferably 10 to 100 microns. Particles of less than 1 micron in diameter can be produced via the present invention, should that size be found to be desirable for fuel injection. The particles of any given aerosol fuel will have about the same diameter with a relative standard deviation of 10% to 30% or more preferably 3% to 20%. Stating that particles of the aerosol have a particle diameter in a range of 10 to 100 microns does not mean that different particles will have different diameters and that some will have a diameter of 10 microns while others of 100 microns. The particles in a given aerosol will all (preferably about 90% or more) have the same diameter ±3% to ±30%. For example, the particles of a given aerosol will have a diameter of 25 microns ±3% to ±10%.

Such a monodisperse aerosol is created using the components and configuration as described above. However, other components and configurations will occur to those skilled in the art. The object of each design will be to supply formulation so that it creates a stable capillary microjet which is accelerated and stabilized by tangential viscous stress exerted by the gas on the liquid surface. The stable microjet created by the gas leaves the area of the pressurized gas (e.g., leaves the pressure chamber and exits the pressure chamber orifice) and splits into particles which have the desired size and uniformity.

The aerosol created is a monodisperse aerosol meaning that the size of the particles produced are relatively uniform in size. The relative standard deviation in particle size is in the range of from about 10% to about 30%, preferably 3% to 10% and most preferably 3% or less. The size of aerosolized particles useful for combustion may range anywhere from 10 nm to 10 microns.

For purposes of simplicity the remainder of the detailed description of the operation of the device of FIGS. 1A and 1B will refer to the first fluid as liquid and the second fluid as gas. The parameter window used (i.e. the set of special values for the liquid properties, flow-rate used, feeding needle diameter, orifice diameter, pressure ratio, etc.) should be large enough to be compatible with virtually any liquid (dynamic viscosities in the range from $10^{-4}$ to 1 kg m$^{-1}$s$^{-1}$); in this way, the capillary microjet that emerges from the end of the feeding needle is absolutely stable and perturbations produced by breakage of the jet cannot travel upstream. Downstream, the microjet splits into evenly shaped drops simply by effect of capillary instability (see, for example, Rayleigh, "On the instability of jets", Proc. London Math. Soc., 4–13, 1878), similar in a manner to a laminar capillary jet falling from a half-open tap.

When the stationary, steady interface is created, the capillary jet that emerges from the end of the drop at the outlet of the feeding point is concentrically withdrawn into the nozzle. After the jet emerges from the drop, the liquid is accelerated by tangential sweeping forces exerted by the gas stream flowing on its surface, which gradually decreases the jet cross-section. Stated differently the gas flow acts as a lens and focuses and stabilizes the microjet as it moves toward and into the exit orifice of the pressure chamber.

The forces exerted by the second fluid (e.g., a gas) flow on the first fluid (e.g., a liquid) surface should be steady enough to prevent irregular surface oscillations. Therefore, any turbulence in the gas motion should be avoided, even if the gas velocity is high, the characteristic size of the orifice should ensure that the gas motion is laminar (similar to the boundary layers formed on the jet and on the inner surface of the nozzle or hole).

Stable Capillary Microjet

Figure 4:
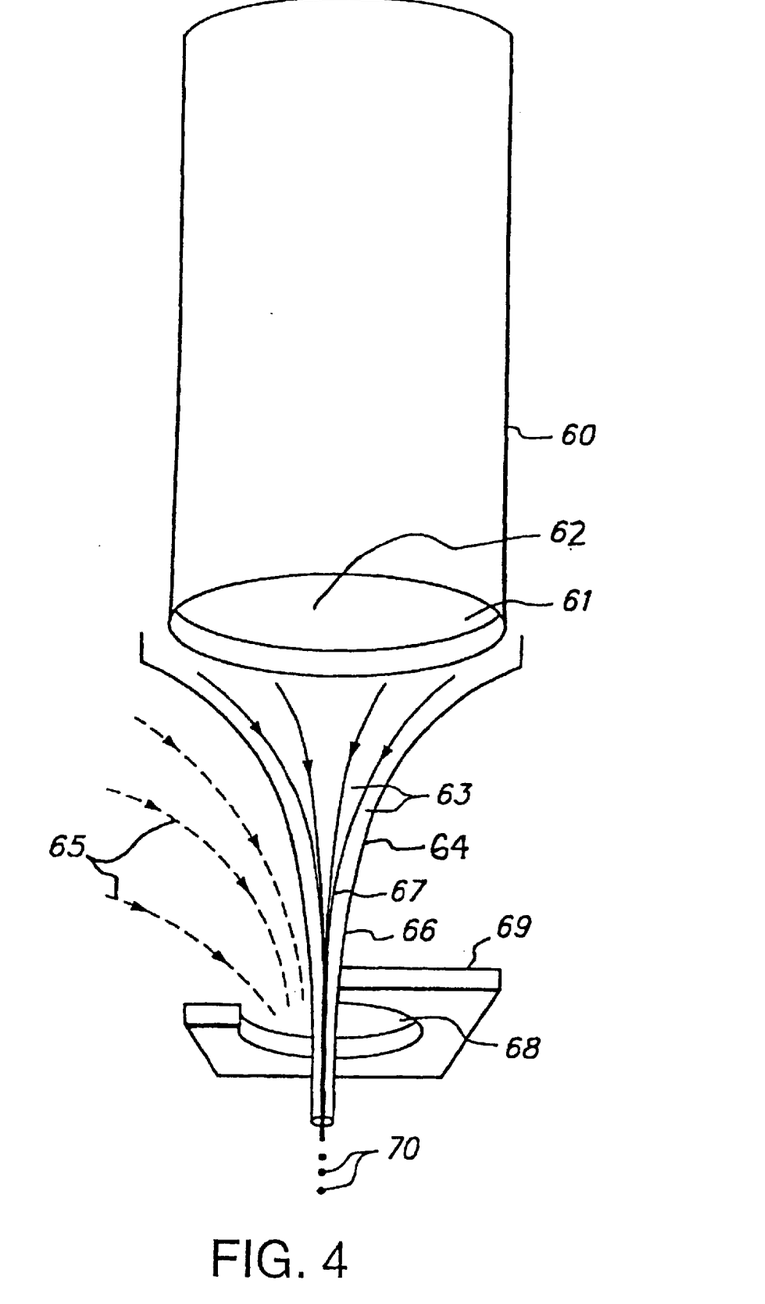
Figure 5:
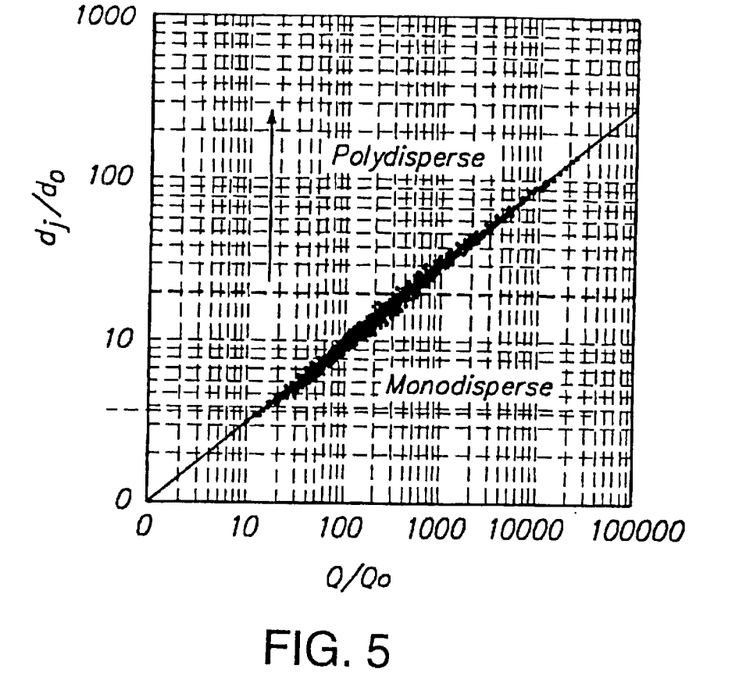

FIG. 4 illustrates one example of the interaction of a liquid and a gas to form atomizate using the method of the invention. The feeding needle 60 has a circular exit opening 61 with an internal radius $R_0$ which feeds a liquid 62 out of the end, forming a drop with a radius in the range of $R_0$ to $R_0$ plus the thickness of the wall of the needle. The exiting liquid forms an infinite amount of liquid streamlines 63 that interact with the surrounding gas to form a stable cusp at the interface 64 of the two fluids. The surrounding gas also forms an infinite number of gas streamlines 65, which interact with the exiting liquid to create a virtual focusing funnel 66. The exiting liquid is focused by the focusing funnel 66 resulting in a stable capillary microjet 67, which remains stable until it exits the opening 68 of the pressure chamber 69. After exiting the pressure chamber, the microjet begins to break-up, forming monodispersed particles 70.

The gas flow, which affects the liquid withdrawal and its subsequent acceleration after the jet is formed, should be very rapid but also uniform in order to avoid perturbing the fragile capillary interface (the surface of the drop that emerges from the jet).

Liquid flows out of the end of a capillary tube and forms a small liquid drop at the end. The tube has an internal radius $R_o$. The drop has a radius in a range of from $R_o$ to $R_o$ plus the structural thickness of the tube as the drop exits the tube, and thereafter the drop narrows in circumference to a much smaller circumference as is shown in the expanded view of the tube (i.e. feeding needle) 5 as shown in FIGS. 1A, 1B and 4.

As illustrated in FIG. 4, the exit opening 61 of the capillary tube 60 is positioned close to an exit opening 68 in a planar surface of a pressure chamber 69. The exit opening 68 has a minimum diameter D and is in a planar member with a thickness L. The diameter D is referred to as a minimum diameter because the opening may have a conical configuration with the narrower end of the cone positioned closer to the source of liquid flow. Thus, the exit opening may be a funnel-shaped nozzle although other opening configurations are also possible, e.g. an hour glass configuration. Gas in the pressure chamber continuously flows out of the exit opening. The flow of the gas causes the liquid drop expelled from the tube to decrease in circumference as the liquid moves away from the end of the tube in a direction toward the exit opening of the pressure chamber.

In actual use, it can be understood that the opening shape which provokes maximum gas acceleration (and consequently the most stable cusp and microjet with a given set of parameters) is a conically shaped opening in the pressure chamber. The conical opening is positioned with its narrower end toward the source of liquid flow.

The distance between the end 61 of the tube 60 and the beginning of the exit opening 68 is H. At this point it is noted that $R_o$, D, H and L are all preferably on the order of hundreds of microns. For example, $R_o$=400 $\mu$m, D=150 $\mu$m, H=1 mm, L=300 $\mu$m. However, each could be 1/100 to 100×these sizes.

The end of the liquid stream develops a cusp-like shape at a critical distance from the exit opening 68 in the pressure chamber 69 when the applied pressure drop $\Delta P_g$ across the exit opening 68 overcomes the liquid-gas surface tension stresses $\gamma/R^*$ appearing at the point of maximum curvature—e.g. $1/R^*$ from the exit opening.

A steady state is then established if the liquid flow rate Q ejected from the drop cusp is steadily supplied from the capillary tube. This is the stable capillary cusp which is an essential characteristic of the invention needed to form the stable microjet. More particularly, a steady, thin liquid jet with a typical diameter $d_j$ is smoothly emitted from the stable cusp-like drop shape and this thin liquid jet extends over a distance in the range of microns to millimeters. The length of the stable microjet will vary from very short (e.g. 1 micron) to very long (e.g. 50 mm) with the length depending on the (1) flow-rate of the liquid and (2) the Reynolds number of the gas stream flowing out of the exit opening of the pressure chamber. The liquid jet is the stable capillary microjet obtained when supercritical flow is reached. This jet demonstrates a robust behavior provided that the pressure drop $\Delta P_g$ applied to the gas is sufficiently large compared to the maximum surface tension stress (on the order of $\gamma/d_j$) that act at the liquid-gas interface. The jet has a slightly parabolic axial velocity profile which is, in large part, responsible for the stability of the microjet. The stable microjet is formed without the need for other forces, i.e. without adding force such as electrical forces on a charged fluid. However, for some applications it is preferable to add charge to particles, e.g. to cause the particles to adhere to a given surface. The shaping of liquid exiting the capillary tube by the gas flow forming a focusing funnel creates a cusp-like meniscus resulting in the stable microjet. This is a fundamental characteristic of the invention.

The fluid stream flowing from the tube has substantially more density and develops substantially more inertia as compared to the gas, which has lower viscosity than the liquid. These characteristics contribute to the formation of the stable capillary jet. The stable capillary microjet is maintained stably for a significant distance in the direction of flow away from the exit from the tube. The liquid is, at this point, undergoing "supercritical flow." The microjet eventually destabilizes due to the effect of surface tension forces. Destabilization results from small natural perturbations moving downstream, with the fastest growing perturbations being those which govern the break up of the microjet, eventually creating a uniform sized monodisperse aerosol 70 as shown in FIG. 4.

The microjet, even as it initially destabilizes, passes out of the exit orifice of the pressure chamber without touching the peripheral surface of the exit opening. This provides an important advantage of the invention which is that the exit opening 68 (which could be referred to as a nozzle) will not clog from residue and/or deposits of the liquid. Clogging is a major problem with very small nozzles and is generally dealt with by cleaning or replacing the nozzle. When fluid contacts the surfaces of a nozzle opening some fluid will remain in contact with the nozzle when the flow of fluid is shut off. The liquid remaining on the nozzle surface evaporates leaving a residue. After many uses over time the residue builds up and clogging takes place. The present invention substantially reduces or eliminates this clogging problem.

Mathematics of a Stable Microjet

Cylindrical coordinates (r,z) are chosen for making a mathematical analysis of a stable microjet, i.e. liquid undergoing "supercritical flow." The cusp-like meniscus formed by the liquid coming out of the tube is pulled toward the exit of the pressure chamber by a pressure gradient created by the flow of gas.

The cusp-like meniscus formed at the tube's mouth is pulled towards the hole by the pressure gradient created by the gas stream. From the cusp of this meniscus, a steady liquid thread with the shape of radius r=ξ is withdrawn through the hole by the action of both the suction effect due to $\Delta P_g$, and the tangential viscous stresses $\tau_s$ exerted by the gas on the jet's surface in the axial direction. The averaged momentum equation for this configuration may be written:

$$\frac{d}{d_z}\left[P_1 + \frac{\rho_1 Q^2}{2\Pi^2 \xi^4}\right] = \frac{2\tau_s}{\xi}, \tag{1}$$

where Q is the liquid flow rate upon exiting the feeding tube, $P_l$ is the liquid pressure, and $\rho_l$ is the liquid density, assuming that the viscous extensional term is negligible compared to the kinetic energy term, as will be subsequently justified. In addition, liquid evaporation effects are neglected. The liquid pressure $P_1$ is given by the capillary equation.

$$P_l = P_g + \gamma/\xi. \tag{2}$$

where γ is the liquid-gas surface tension. As shown in the Examples, the pressure drop $\Delta P_g$ is sufficiently large as compared to the surface tension stress γ/ξ to justify neglecting the latter in the analysis. This scenario holds for the whole range of flow rates in which the microjet is absolutely stable. In fact, it will be shown that, for a given pressure drop $\Delta P_g$, the minimum liquid flow rate that can be sprayed in steady jet conditions is achieved when the surface tension stress γ/ξ is of the order of the kinetic energy of the liquid $\rho_1 Q^2/(2\pi^2 \xi^4)$, since the surface tension acts like a "resistance" to the motion (it appears as a negative term in the right-hand side term of Eq. (1)). Thus, $$Q_{min} \sim \left(\frac{\gamma d_j^3}{\rho_1}\right)^{\frac{1}{2}} \tag{3}$$

For sufficiently large flow rates Q compared to $Q_{min}$, the simplified averaged momentum equation in the axial direction can be expressed as $$\frac{d}{d_z}\left(\frac{\rho_1 Q^2}{2\Pi^2 \xi^4}\right) = \frac{dP_g}{d_z} + \frac{2\tau_s}{\xi}, \tag{4}$$

where one can identify the two driving forces for the liquid flow on the right-hand side. This equation can be integrated provided the following simplification is made: if one uses a thin plate with thickness L of the order or smaller than the hole's diameter D (which minimizes downstream perturbations in the gas flow), the pressure gradient up to the hole exit is on the average much larger than the viscous shear term $2\tau_s/\xi$ owning to the surface stress. On the other hand, the axial viscous term is of the order $O[\mu^2 Q/D^2 d_j^2]$, since the hole diameter D is actually the characteristic distance associated with the gas flow at the hole's entrance in both the radial and axial directions. This term is very small compared to the pressure gradient in real situations, provided that $\Delta P_g >> \mu^2/D^2 \rho_1$ (which holds, e.g., for liquids with viscosities as large as 100 cpoises, using hole diameters and pressure drops as small as D~10 μm and $\Delta P_g \geq 100$ mbar). The neglect of all viscous terms in Eq. (4) is then justified. Notice that in this limit on the liquid flow is quasi-isentropic in the average (the liquid almost follows Bernoulli equation) as opposed to most micrometric extensional flows. Thus, integrating (4) from the stagnation regions of both fluids up to the exit, one obtains a simple and universal expression for the jet diameter at the hole exit:

$$d_j \simeq \left(\frac{8\rho_1}{\Pi^2 \Delta P_g}\right)^{\frac{1}{4}} Q^{\frac{1}{2}}, \tag{5}$$

which for a given pressure drop $\Delta P_g$ is independent of geometrical parameters (hole and tube diameters, tube-hole distance, etc.), liquid and gas viscosities, and liquid-gas surface tension. This diameter remains almost constant up to the breakup point since the gas pressure after the exit remains constant.

Monodisperse Particles

Above the stable microjet undergoing "supercritical flow" is described and it can be seen how this aspect of the invention can be made use of in a variety of industrial applications—particularly where the flow of liquid through small holes creates a clogging problem. An equally important aspect of the invention is obtained after the microjet leaves the pressure chamber.

When the microjet exits the pressure chamber the liquid pressure $P_l$ becomes (like the gas pressure $P_g$) almost constant in the axial direction, and the jet diameter remains almost constant up to the point where it breaks up by capillary instability. Defining a Weber number We= $(\rho_g v_g^2 d_j)/\gamma \simeq 2\Delta P_g d_j/\gamma$ (where $v_g$ is the gas velocity measured at the orifice), below a certain experimental value $We_c$~40 the breakup mode is axisymmetric and the resulting droplet stream is characterized by its monodispersity provided that the fluctuations of the gas flow do not contribute to droplet coalescence (these fluctuations occur when the gas stream reaches a fully developed turbulent profile around the liquid jet breakup region). Above this $We_c$ value, sinuous nonaxisymmetric disturbances, coupled to the axisymmetric ones, become apparent. For larger We numbers, the nonlinear growth rate of the sinuous disturbances seems to overcome that of the axisymmetric disturbances. The resulting spray shows significant polydispersity in this case. Thus, it can be seen that by controlling parameters to keep the resulting Weber number to 40 or less, allows the particles formed to be all substantially the same size. The size variation is about ±3% to ±30% and move preferably ±3% to ±10%. These particles can have a desired size e.g. 0.1 microns to 50 microns.

The shed vorticity influences the breakup of the jet and thus the formation of the particles. Upstream from the hole exit, in the accelerating region, the gas stream is laminar. Typical values of the Reynolds number range from 500 to 6000 if a velocity of the order of the speed of sound is taken as characteristic of the velocity of the gas. Downstream from the hole exit, the cylindrical mixing layer between the gas stream and the stagnant gas becomes unstable by the classical Kelvin-Helmholtz instability. The growth rate of the thickness of this layer depends on the Reynolds number of the flow and ring vortices are formed at a frequency of the order of $v_g/D$, where D is the hole diameter. Typical values of $v_g$ and D as those found in our experimental technique lead to frequencies or the order of MHz which are comparable to the frequency of drop production (of order of $t_b^{-1}$).

Given the liquid flow rate and the hole diameter, a resonance frequency which depends on the gas velocity (or pressure difference driving the gas stream) can be adjusted (tuned) in such a way that vortices act as a forcing system to excite perturbations of a determined wavelength on the jet surface. Experimental results obtained clearly illustrates the different degree of coupling between the two gas-liquid coaxial jets. In one set of experimental results the particle sizes are shown to have a particle size of about 5.7 microns with a standard deviation of 12%. This results when the velocity of the gas has been properly tuned to minimize the dispersion in the size of droplets resulting from the jet breakup. In this case, the flow rate of the liquid jet and its diameter are 0.08 $\mu$l s$^{-1}$ and 3 $\mu$m, respectively. Data have been collected using a MASTERSIZER from MALVERN Instruments. As the degree of coupling decreases, perturbations at the jet surface of different wavelengths become excited and, as it can be observed from the size distributions, the dispersion of the spray increases.

It is highly desirable in a number of different industrial applications to have particles which are uniform in size or to create aerosols of liquid particles which are uniform in size. For example, particles of a liquid formation containing a hydrocarbon could be created and designed to have a diameter of about 10 microns ±3%. These particles could be injected into the combustion chamber of an engine. Moreover, particle size can be adjusted to increase fuel efficiency, thus wasting less fuel in the combustion reaction.

The gas flow should be laminar in order to avoid a turbulent regime—turbulent fluctuations in the gas flow which have a high frequency and would perturb the liquid-gas interface. The Reynolds numbers reached at the orifice are $$Re = \frac{v_g d_0}{v_g} \sim 4000$$

where $v_g$ is the kinematic viscosity of the gas. Even though this number is quite high, there are large pressure gradients downstream (a highly convergent geometry), so that a turbulent regime is very unlikely to develop.

The essential difference from existing pneumatic atomizers (which possess large Weber numbers) and the present invention is that the aim of the present invention is not to rupture the liquid-gas interface but the opposite, i.e. to increase the stability of the interface until a capillary jet is obtained. The jet, which will be very thin provided the pressure drop resulting from withdrawal is high enough, splits into drops the sizes of which are much more uniform than those resulting from disorderly breakage of the liquid-gas interface in existing pneumatic atomizers.

The proposed fuel injection nozzle system obviously requires delivery of the fuel to be aerosolized and the gas to be used in the resulting spray. Both should be fed at a rate ensuring that the system lies within the stable parameter window. Multiplexing is effective when the flow-rates needed exceed those on an individual cell. More specifically, a plurality of feeding sources or feeding needles may be used to increase the rate at which aerosols are created. The flow-rates used should also ensure the mass ratio between the flows is compatible with the specifications of each application.

The gas and liquid can be dispensed by any type of continuous delivery system (e.g. a compressor or a pressurized valve system. If multiplexing is needed, the liquid flow-rate should be as uniform as possible among cells; this may entail propulsion through several capillary needles, porous media or any other medium capable of distributing a uniform flow among different feeding points.

Each individual injection nozzle should consist of at least one feeding point (a capillary needle, a point with an open microchannel, a microprotuberance on a continuous edge, etc.) 0.002–2 mm (but, preferentially 0.01–1.2 mm) in diameter, where the drop emerging from the microjet can be anchored, and a small orifice 0.002–2 mm (preferentially 0.01–1.0 mm) in diameter facing the drop and separated 0.01–2 mm (preferentially 0.2–0.75 mm) from the feeding point. The orifice communicates the withdrawal gas around the drop, at an increased pressure, with the zone where the atomizate is produced, at a decreased pressure. The injection nozzle can be made from a variety of materials (but preferably a material that is not reactive with fuel, metal, polymers, etc.).

FIGS. 1A and 1B depicts a tested prototype where the liquid to be atomized is inserted through one end of the system 2 and the gas in introduced via the special inlet 4 in the pressure chamber 3. The prototype was tested at gas feeding rates from 100 to 2000 mBar above the atmospheric pressure $P_a$ at which the atomized liquid was discharged. The whole enclosure around the feeding needle 1 was at a pressure $P_0 > P_a$. The liquid feeding pressure, $P_l$, should always be slightly higher than the gas propelling pressure, $P_0$. Depending on the pressure drop in the needle and the liquid feeding system, the pressure difference ($P_l - P_0 > 0$) and the flow-rate of the liquid to be atomized, Q, are linearly related provided the flow is laminar—which is indeed the case with this prototype. The critical dimensions are the distance from the needle to the plate (H), the needle diameter ($D_0$), the diameter of the orifice through which the microjet 6 is discharged ($d_0$) and the axial length, e, of the orifice (i.e. the thickness of the plate where the orifice is made). In this prototype, H was varied from 0.3 to 0.7 mm on constancy of the distances ($D_0$=0.45 mm, $d_0$–0.2 mm) and e–0.5 mm. The quality of the resulting spray 7 did not vary appreciably with changes in H provided the operating regime (i.e. stationary drop and micro jet) was maintained. However, the system stability suffered at the longer H distances (about 0.7 mm). The other atomizer dimensions had no effect on the spray or the prototype functioning provided the zone around the needle (its diameter) was large enough relative to the feeding needle.

Weber Number

Adjusting parameters to obtain a stable capillary microjet and control its breakup into monodisperse particle is governed by the Weber number and the liquid-to-gas velocity ratio or α which equal $V_l/V_g$. The Weber number or "We" is defined by the following equation:

$$We = \frac{\rho_g V_g^2 d}{\gamma}$$

wherein $\rho_g$ is the density of the gas, d is the diameter of the stable microjet, $\gamma$ is the liquid-gas surface tension, and $V^{g2}$ is the velocity of the gas squared.

When carrying out the invention the parameters should be adjusted so that the Weber number is greater than 1 in order to produce a stable capillary microjet. However, to obtain a particle dispersion which is monodisperse (i.e. each particle has the same size ±3 to ±30%) the parameters should be adjusted so that the Weber number is less than 40. The monodisperse aerosol is obtained with a Weber number in a range of about 1 to about 40 when the breaking time is sufficiently small to avoid non-symmetric perturbations. ($1 \leqq We \leqq 40$)

Ohnesorge Number

A measure of the relative importance of viscosity on the jet breakup can be estimated from the Ohnesorge number defined as the ratio between two characteristic times: the viscous time $t_v$ and the breaking time $t_b$. The breaking time $t_b$ is given by [see Rayleigh (1878)]

$$t_b \sim \left(\frac{\rho_l d^2}{\gamma}\right)^{\frac{1}{2}}. \quad (2)$$

Perturbations on the jet surface are propagated inside by viscous diffusion in times $t_v$ of the order of $$t_v \sim \rho_l d^2/\mu_1, \quad (3)$$

where $\mu_l$ is the viscosity of the liquid. Then, the Ohnesorge number, Oh, results $$Oh = \frac{\mu_1}{(\rho_l \gamma d)^{\frac{1}{2}}}. \quad (4)$$

If this ratio is much smaller than unity viscosity plays no essential role in the phenomenon under consideration. Since the maximum value of the Ohnesorge number in actual experiments conducted is as low as $3.7\times10^{-1}$, viscosity plays no essential role during the process of jet breakup.

Formation of the microjet and its acceleration and ultimate particle formation are based on the abrupt pressure drop associated with the steep acceleration experienced by the first fluid (e.g., a gas) on passing through an exit orifice of the pressure chamber which holds the second fluid. On leaving the chamber the flow undergoes a large pressure difference between the first fluid (e.g., a liquid) and the second fluid (e.g., a gas), which in turn produces a highly curved zone on the first fluid (e.g., liquid) surface near the exit port of the pressure chamber and in the formation of a cuspidal point from which a steady microjet flows provided the amount of the first fluid (e.g., liquid) withdrawn through the exit port of the pressure chamber is replenished. Thus, in the same way that a glass lens or a lens of the eye focuses light to a given point the flow of the gas surrounds and focuses the liquid into a stable microjet. The focusing effect of the surrounding flow of gas creates a stream of liquid which is substantially smaller in diameter than the diameter of the exit orifice of the pressure chamber. This allows liquid to flow out of the pressure chamber orifice without touching the orifice. This provides advantages including (1) clogging of the exit orifice is virtually eliminated, (2) contamination of flow due to contact with substances on the orifice opening is virtually eliminated. (3) the diameter of the stream and thus the resulting particles is smaller than the diameter of the exit orifice of the chamber, (4) the particles are not prone to agglomeration following exit from the chamber. This is particularly desirable because it is difficult to precisely engineer holes which are very small in diameter. Further, in the absence of the focusing effect a flow of liquid out of an opening will result in particles which have about twice the diameter of the exit opening.

In summary, the fluid 2 flow, which effects the liquid withdrawal and its subsequent acceleration after the jet is formed, should be very rapid, but also uniform, in order to avoid perturbing the fragile capillary interface (the surface of the drop that emerges from the jet) and hence its breaking. Therefore, the dynamic forces exerted by the fluid 2 should never exceed the surface tension (drop and microjet) at any time during the process. In terms of non-dimensional fluid dynamics numbers, the Weber number (i.e. the dynamic to surface tension force ratio) should not exceed unity during the process. The Weber number for the microjet will inevitably be unity because the pressure drop in the fluid 2 is similar in magnitude to the effect of the surface tension:

$$\frac{2\gamma}{d_j} \sim \frac{1}{2}\rho v_g^2$$

where γ and ρ are the surface tension and liquid density, respectively; and $d_j$ and $v_g$ are the characteristic diameter of the jet and characteristic velocity of the fluid 2. Also, the velocity of the fluid 2 around the drop that produces the jet must be related to that across the orifice via the areas, i.e. $V_g D_0^2 \sim v_g d_0^2$, where $V_g$ is the velocity of the fluid 2 around the drop, and $D_0$ and $d_0$ are the diameters of the feeding point and orifice, respectively. Since the maximum possible fluid 2 velocity at the orifice is similar to the speed of sound, one has $$V_g \sim \left(\frac{d_0}{D_0}\right)^2 \times 320 \text{ m/s}$$

and, for the jet diameter, $$d_j \sim \frac{4\gamma}{\rho_g v_g^2} \sim \frac{4 \cdot 2 \cdot 10^2}{1.2 \times 320^2} \sim 5\ \mu\text{m}\ (\gamma \sim 2 \cdot 10^2\ N/m^2 \text{ for } n\text{-heptane})$$

This indicates that micrometric drop sizes in the range of 1 to 10 microns in diameter or even less than 1 micron in diameter can be obtained.

At the smallest diameters possible with this system (similar to the thickness of the boundary layer), the kinetic energies per unit volume of the liquid and fluid 2 should be of the same order. The resulting liquid velocity will be $$V_l \sim \left(\frac{\rho_g}{\rho_1}\right)^{\frac{1}{2}} v_g \sim 10 \text{ m/s}$$

where $\rho_1$ is the liquid density. From the previous equation, the liquid flow-rate turns out to be $$Q_l \sim d_j^2 v_l \sim 10^{-11} m^3/s$$

at the smallest drop sizes.

The fluid 2 flow should be laminar in order to avoid a turbulent regime—turbulent fluctuations in the fluid 2 flow, which has a high frequency, would perturb the liquid-fluid 2 interface. The Reynolds numbers reached at the orifice are $$Re = \frac{v_g d_0}{v_g} \sim 4000$$

where $v_g$ is the kinematic viscosity of the fluid 2. Even though this number is quite high, there are large pressure gradients downstream (a highly convergent geometry), so a turbulent regime is very unlikely to develop.

The essential difference from existing pneumatic atomizers (which possess large Weber numbers) is that the aim is not to rupture the liquid-fluid 2 interface but the opposite, i.e. to increase the stability of the interface until a capillary jet is obtained. The jet, which will be very thin provided the pressure drop resulting from withdrawal is high enough, splits into drops the sizes of which are much more uniform than those resulting from disorderly breakage of the liquid-fluid 2 interface in existing pneumatic atomizers.

Exemplary Uses of the First Embodiment

The first embodiment of the invention can be employed in a nozzle-type injection device to inject a more fine and evenly distributed liquid particle, e.g. to an internal combustion chamber. Since each injection will involve the injection a relatively small volume of liquid, due to the fine nature of the particles formed, it is desirable to have multiple injection points in each device. Accordingly, the device may have a plurality of feeding needles in a single injection device, preferably at least 10, more preferably at least 100, even more preferably at least 500, and even more preferably at least 1000. The injection points may be spatially arranged in the device in any manner that allows the efficient production of particles, and preferably the injection points are arranged in a configuration to decrease the tendency for agglomeration once the particles enter the combustion chamber, e.g. evenly spaced in a parallel manner in the device. The gas and liquid used for fuel can be dispensed to the feeding needles by any type of continuous delivery system, e.g. a compressor or a pressurized tank for gas delivery and a volumetric pump or a pressurized bottle the latter for liquid delivery. The dispersion of the gas and/or liquid may be controlled using any mechanism known in the art, for example through the use of a valve that controls the entrance of the gas and/or liquid into the inlet tubes leading to the injection device. The housing of the device and the feeding needle can be made from a variety of materials (metal, plastic, ceramics, glass), and preferably from materials that do not react with the fluids used in the device.

Figure 6A:
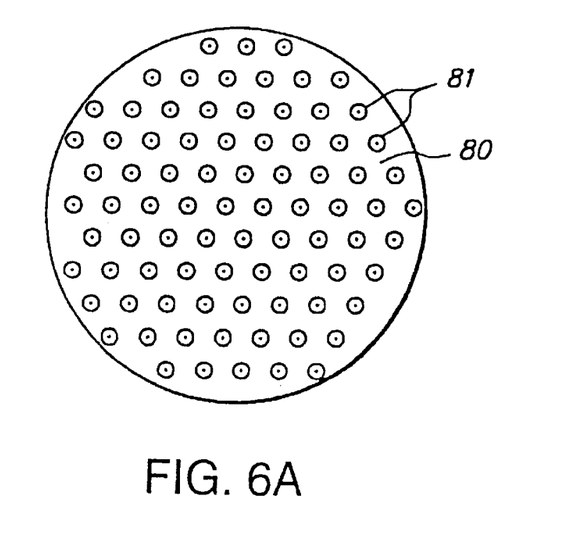

FIG. 6 illustrates a generalized, schematic view of an exemplary use of the embodiment of FIGS. 1A and 1B in an injection apparatus. In the device of FIG. 6, a plurality of evenly spaced feeding needles 84 are housed in a pressure chamber 80, and the fuel is atomized multiple exit openings 81 in the pressure chamber 80. FIG. 6A is a side view of the internal portion of the device, with multiple injection needles 84 housed inside a single pressure chamber 80. The pressure chamber should be such that the pressure is approximately equivalent throughout the chamber, allowing the efficient production of stable focusing cusps for each separate feeding needle. Alternatively, each feeding needle could have its own, compartmentalized pressure chamber, with each chamber individually controlled to have approximately equal pressure and in-flow of fluid.

The fuel is supplied to the feeding needles through an inlet opening 82, and the in-flow of fuel is preferably controlled by a mechanism within the fuel in injector, e.g. a valve controllably opened by the use of a computer signal to the fuel injector. See e.g. U.S. Pat. Nos. 4,984,552 and 5,697,341 which are both incorporated herein by reference. In the example of FIG. 6, the fuel is supplied to each separate needle from a single source via a fuel feeding tube 83 positioned above and connected to each of the feeding needles 84. Other methods of introducing fuel to the individual feeding needles, such as separate fuel feeding tubes stemming from either a single fuel source or multiple fuel sources, can also be employed. Should multiple sources be employed, they are preferably synchronized and/or modulated to control of the quantity of fuel injected.

Figure 6B:
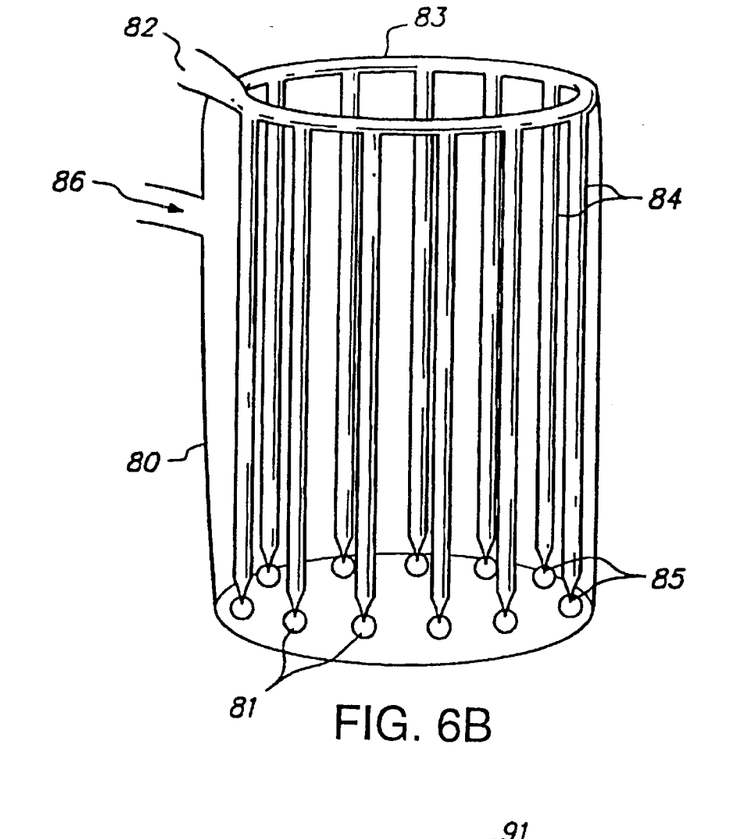

The second fluid used to focus the first is provided through at least one separate inlet opening 86. FIG. 6B is a view from the bottom of the device, showing the multiple exit openings 81 in the pressure chamber 80. Although FIG. 6 illustrates a single pressure chamber, multiple pressure chambers may be used to increase the efficiency of the device. Fluid to these separate chambers may be provided from a single outlet source, or from multiple sources.

In another example of the embodiment of FIGS. 1A and 1B, the fuel may be provided as the second fluid of the invention, and a gas, preferably air, is used as the first fluid. The gas is then fed through the feeding needles, with the fuel formulation introduced into the pressure chamber. The fuel is used to focus the gas, and the gas is expelled in particle form. The fuel, as the second fluid will coat the gas particles as the fluids exit the pressure chamber. Expulsion of the gas bubbles contained in the liquid stream into a gaseous environment results in the production of highly disperse fuel globules with a gas core, preferably an air core. This use of the injection nozzle may increase the surface area of the fuel formulation available for reaction while conserving the fuel composition.

Embodiment of FIG. 2

A variety of configurations of components and types of fluids will become apparent to those skilled in the art upon reading this disclosure. These configurations and fluids are encompassed by the present invention provided they can produce a stable capillary microjet of a first fluid from a source to an exit port of a pressure chamber containing a second fluid. The stable microjet is formed by the first fluid flowing from the feeding source to the exit port of the pressure chamber being accelerated and stabilized by tangential viscous stress exerted by the second fluid in the pressure chamber on the surface of the first fluid forming the microjet. The second fluid forms a focusing funnel when a variety of parameters are correctly tuned or adjusted. For example, the speed, pressure, viscosity and miscibility of the first and second fluids are chosen to obtain the desired results of a stable microjet of the first fluid focused into the center of a funnel formed with the second fluid. These results are also obtained by adjusting or tuning physical parameters of the device, including the size of the opening from which the first fluid flows, the size of the opening from which both fluids exit, and the distance between these two openings.

The embodiment of FIGS. 1A and 1B can, itself, be arranged in a variety of configurations. Further, as indicated above, the embodiment may include a plurality of feeding needles. A plurality of feeding needles may be configured concentrically in a single construct, as shown in FIG. 2.

The components of the embodiment of FIG. 2 are as follows:

21. Feeding needle—tube or source of fluid.
22. End of the feeding needle used to insert the liquids to be atomized.
23. Pressure chamber.
24. Orifice used as gas inlet.
25. End of the feeding needle used to evacuate the liquid to be atomized.
26. Orifice through which withdrawal takes place.
27. Atomizate (spray) or aerosol.
28. First liquid to be atomized (inner core of particle).
29. Second liquid to be atomized (outer coating of particle).
30. Gas for creation of microjet.
31. Internal tube of feeding needle.
32. External tube of feeding needle.

D=diameter of the feeding needle; d=diameter of the orifice through which the microjet is passed; e=axial length of the orifice through which withdrawal takes place; H=distance from the feeding needle to the microjet outlet; γ=surface tension; $P_0$=pressure inside the chamber: $P_a$=atmospheric pressure.

The embodiment of FIG. 2 is preferably used when attempting to form a spherical particle of one substance coated by another substance. The device of FIG. 2 is comprised of the same basic component as per the device of FIGS. 1A and 1B and further includes a second feeding source 32 which is positioned concentrically around the first cylindrical feeding source 31. The second feeding source may be surrounded by one or more additional feeding sources with each concentrically positioned around the preceding source.

The process is based on the microsuction which the liquid-gas or liquid-liquid interphase undergoes (if both are immiscible), when said interphase approaches a point beginning from which one of the fluids is suctioned off while the combined suction of the two fluids is produced. The interaction causes the fluid physically surrounded by the other to form a capillary microjet which finally breaks into spherical drops. If instead of two fluids (gas-liquid), three or more are used that flow in a concentric manner by injection using concentric tubes, a capillary jet composed of two or more layers of different fluids is formed which, when it breaks, gives rise to the formation of spheres composed of several approximately concentric spherical layers of different fluids. The size of the outer sphere (its thickness) and the size of the inner sphere (its volume) can be precisely adjusted.

The method is based on the breaking of a capillary microjet composed of a nucleus of one liquid or gas and surrounded by another or other liquids and gases which are in a concentric manner injected by a special injection head, in such a way that they form a stable capillary microjet and that they do not mix by diffusion during the time between when the microjet is formed and when it is broken. When the capillary microjet is broken into spherical drops under the proper operating conditions, which will be described in detail below, these drops exhibit a spherical nucleus, the size and eccentricity of which can be controlled.

In the case of spheres containing two materials, the injection head 25 consists of two concentric tubes with an external diameter on the order of one millimeter. Through the internal tube 31 is injected the material that will constitute the nucleus of the microsphere, while between the internal tube 31 and the external tube 32 the coating is injected. The fluid of the external tube 32 joins with the fluid of tube 31 as the fluids exit the feeding needle, and the fluids (normally liquids) thus injected are accelerated by a stream of gas that passes through a small orifice 24 facing the end of the injection tubes. When the drop in pressure across the orifice 24 is sufficient, the liquids form a completely stationary capillary microjet, if the quantities of liquids that are injected are stationary. This microjet does not touch the walls of the orifice, but passes through it wrapped in the stream of gas or funnel formed by gas from the tube 32. Because the funnel of gas focuses the liquid, the size of the exit orifice 26 does not dictate the size of the particles formed.

When the parameters are correctly adjusted, the movement of the liquid is uniform at the exit of the orifice 26 and the viscosity forces are sufficiently small so as not to alter either the flow or the properties of the liquids; for example, if there are biochemical molecular specimens having a certain complexity and fragility, the viscous forces that would appear in association with the flow through a microorifice might degrade these substances.

FIG. 2 shows a simplified diagram of the feeding needle 21, which is comprised of the concentric tubes 30, 31 through the internal and external flows of the fluids 28, 29 that are going to compose the microspheres comprised of two immiscible fluids. The difference in pressures $P_0-P_a$ ($P_0>P_a$) through the orifice 26 establishes a flow of gas present in the chamber 23 and which is going to surround the microjet at its exit. The same pressure gradient that moves the gas is the one that moves the microjet in an axial direction through the hole 26, provided that the difference in pressures $P_0-P_a$ is sufficiently great in comparison with the forces of surface tension, which create an adverse gradient in the direction of the movement.

There are two limitations for the minimum sizes of the inside and outside jets that are dependent (a) on the surface tensions γ1 of the outside liquid 29 with the gas 30 and γ2 of the outside liquid 29 with the inside liquid 28, and (b) on the difference in pressures $\Delta P=P_0-P_a$ through the orifice 26. In the first place, the jump in pressures $\Delta P$ must be sufficiently great so that the adverse effects of the surface tension are minimized. This, however, is attained for very modest pressure increases: for example, for a 10 micron jet of a liquid having a surface tension of 0.05 N/m (tap water), the necessary minimum jump in pressure is in the order of 0.05 (N/m)/0.00001 m=$\Delta P$=50 mBar. But, in addition, the breakage of the microjet must be regular and axisymmetric, so that the drops will have a uniform size, while the extra pressure $\Delta P$ cannot be greater than a certain value that is dependent on the surface tension of the outside liquid with the gas γ1 and on the outside diameter of the micro jet. It has been experimentally shown that this difference in pressures cannot be greater than 20 times the surface tension γ1 divided by the outside radius of the microjet.

Therefore, given some inside and outside diameters of the microjet, there is a range of operating pressures between a minimum and a maximum; nonetheless, experimentally the best results are obtained for pressures in the order of two to three times the minimum.

The viscosity values of the liquids must be such that the liquid with the greater viscosity $\mu_{max}$ verifies, for a diameter d of the jet predicted for this liquid and a difference through the orifice $\Delta P$, the inequality:

$$\mu_{max} \leq \frac{\Delta P d^2 D}{Q}$$

With this, the pressure gradients can overcome the extensional forces of viscous resistance exerted by the liquid when it is suctioned toward the orifice.

Moreover, the liquids must have very similar densities in order to achieve the concentricity of the nucleus of the microsphere, since the relation of velocities between the liquids moves according to the square root of the densities $v1/v2=(\rho2/\rho1)^{1/2}$ and both jets, the inside jet and the outside jet, must assume the most symmetrical configuration possible, which does not occur if the liquids have different velocities (FIG. 2). Nonetheless, it has been experimentally demonstrated that, on account of the surface tension $\gamma2$ between the two liquids, the nucleus tends to migrate toward the center of the microsphere, within prescribed parameters.

When two liquids and gas are used on the outside, the distance between the planes of the mouths of the concentric tubes can vary, without the characteristics of the jet being substantially altered, provided that the internal tube 31 is not introduced into the external one 32 more than one diameter of the external tube 32 and provided that the internal tube 31 does not project more than two diameters from the external tube 32. The best results are obtained when the internal tube 31 projects from the external one 32 a distance substantially the same as the diameter of the internal tube 31. This same criterion is valid if more than two tubes are used, with the tube that is surrounded (inner tube) projecting beyond the tube that surrounds (outer tube) by a distance substantially the same as the diameter of the first tube.

The distance between the plane of the internal tube 31 (the one that will normally project more) and the plane of the orifice may vary between zero and three outside diameters of the external tube 32, depending on the surface tensions between the liquids and with the gas, and on their viscosity values. Typically, the optimal distance is found experimentally for each particular configuration and each set of liquids used.

Each atomizing device will consist of concentric tubes 31, 32 with a diameter ranging between 0.05 and 2 mm, preferably between 0.1 and 0.4 mm, on which the drop from which the microjet emanates can be anchored, and a small orifice (between 0.001 and 2 mm in diameter, preferably between 0.1 and 0.25 mm), facing the drop and separated from the point of feeding by a distance between 0.001 and 2 mm, preferably between 0.2 and 0.5 mm. The orifice puts the suction gas that surrounds the drop, at higher pressure, in touch with the area in which the atomizing is to be attained, at lower pressure.

Exemplary Uses of Second Embodiment

The embodiment of the second invention is very similar to that illustrated in FIG. 6, with the difference in that multi-formulation particles may be injected into the combustion chamber. This may allow the surface of a molecule to have a certain component of the overall fuel composition accessible to the surface, with the remaining components of the composition in the nucleus of the liquid particle. For example, in a diesel fuel formulation containing ether, kerosene, castor oil and isopropyl nitrate, it may be desirable to have the kerosene as a coating and the other three molecules in the nucleus of the particle. Accordingly, the formulation containing ether, castor oil and isopropyl nitrate would be introduced into the inner tube of the feeding needle, and the formulation of kerosene (or kerosene dissolved in ether) would be introduced into the external tube of the feeding needle. This would produce an atomization of fuel particles with a kerosene coating, which may increase the surface area available for combustion reaction with the kerosene component of the fuel composition. This embodiment may be used for any fuel composition in which it is desirable to have one or more components of the composition coating the fuel particle and the remaining components positioned in the nucleus of the same particle.

A nozzle-type injection device utilizing the second embodiment would be very similar to FIG. 6, with a plurality of feeding needles positioned within either a single pressure chamber or within multiple pressure chambers. The major difference is that the fuel composition would be introduced to the feeding needle using separate sources for the formulation of the coating of the particle and the formulation of the nucleus of the particle.

Figure 3A:
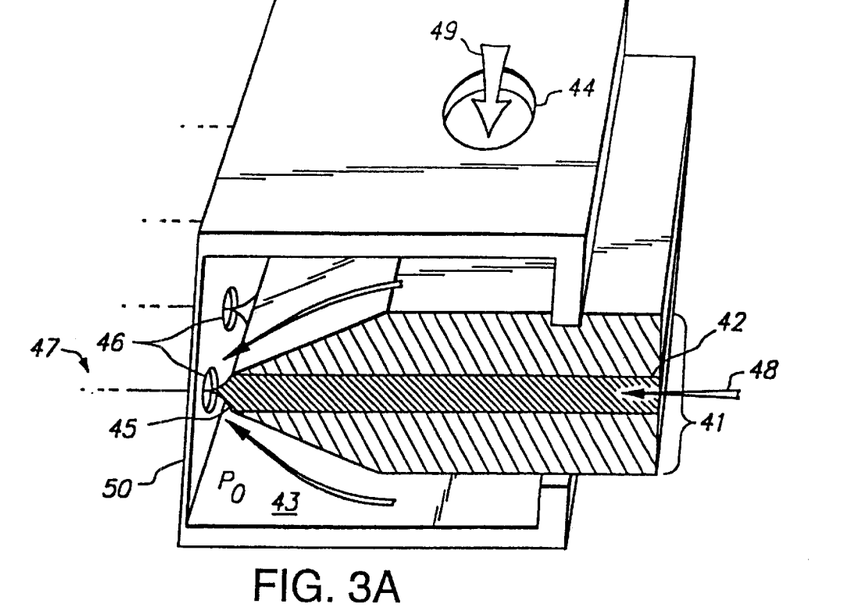
Figure 3B:
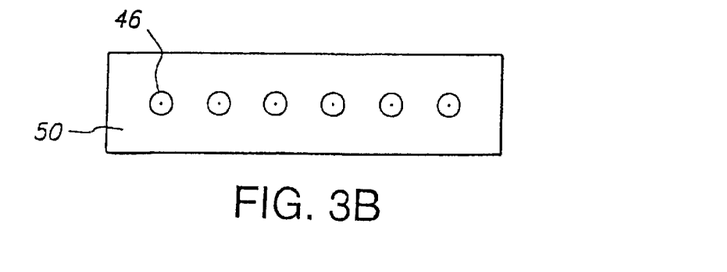
Figure 3C:
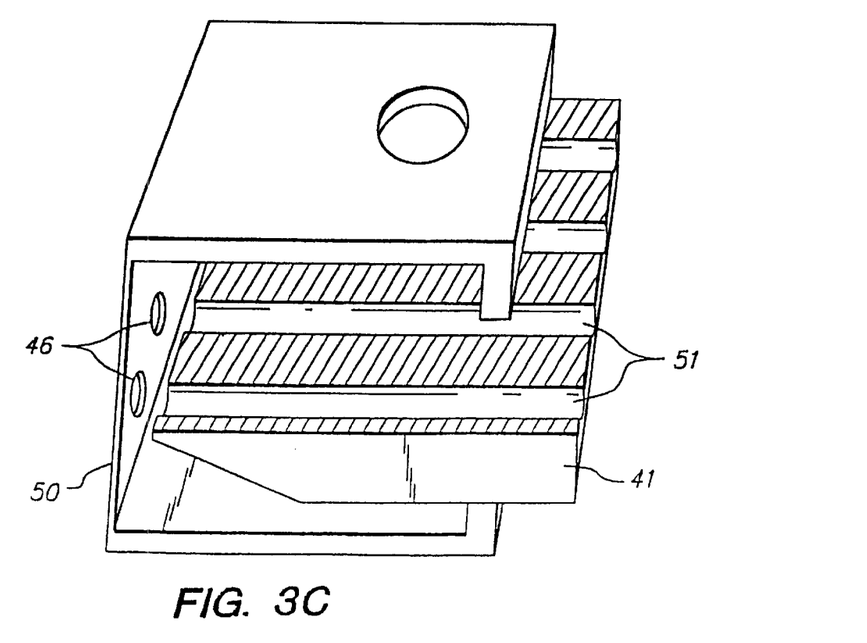

Embodiment of FIG. 3

The embodiments of FIGS. 1A, 1B and 2 are similar in a number of ways. Both have a feeding piece which is preferably in the form of a feeding needle with a circular exit opening. Further, both have an exit port in the pressure chamber which is positioned directly in front of the flow path of fluid out of the feeding source. Precisely maintaining the alignment of the flow path of the feeding source with the exit port of the pressure chamber can present an engineering challenge particularly when the device includes a number of feeding needles. The embodiment of FIG. 3 is designed to simplify the manner in which components are aligned. The embodiment of FIG. 3 uses a planar feeding piece (which by virtue of the withdrawal effect produced by the pressure difference across a small opening through which fluid is passed) to obtain multiple microjets which are expelled through multiple exit ports of a pressure chamber thereby obtaining multiple aerosol streams. Although a single planar feeding member as shown in FIG. 3 it, of course, is possible to produce a device with a plurality of planar feeding members where each planar feeding member feeds fluid to a linear array of outlet orifices in the surrounding pressure chamber. In addition, the feeding member need not be strictly planar, and may be a curved feeding device comprised of two surfaces that maintain approximately the same spatial distance between the two pieces of the feeding source. Such curved devices may have any level of curvature, e.g. circular, semicircular, elliptical, hemi-elliptical, etc.

The components of the embodiment of FIG. 3 are as follows:

41. Feeding piece.
42. End of the feeding piece used to insert the fluid to be atomized.
43. Pressure chamber.
44. Orifice used as gas inlet.
45. End of the feeding needle used to evacuate the liquid to be atomized.
46. Orifices through which withdrawal takes place.
47. Atomizate (spray) or aerosol.
48. first fluid containing material to be atomized.
49. second fluid for creation of microjet.
50. wall of the propulsion chamber facing the edge of the feeding piece.
51. channels for guidance of fluid through feeding piece.

$d_j$=diameter of the microjet formed; $\rho_A$=liquid density of first fluid (48); $\rho_B$=liquid density of second fluid (49); $v_A$=velocity of the first liquid (48); $v_B$=velocity of the second liquid (49); e=axial length of the orifice through which withdrawal takes place; H=distance from the feeding needle to the microjet outlet; $P_0$=pressure inside the chamber;

$\Delta p_g$=change in pressure of the gas; $P_a$=atmospheric pressure; Q=volumetric flow rate The proposed dispersing device consists of a feeding piece 41 which creates a planar feeding channel through which a where a first fluid 48 flows. The flow is preferably directed through one or more channels of uniform bores that are constructed on the planar surface of the feeding piece 41. A pressure chamber 43 that holds the propelling flow of a second liquid 49, houses the feeding piece 41 and is under a pressure above maintained outside the chamber wall 50. One or more orifices, openings or slots (outlets) 46 made in the wall 52 of the propulsion chamber face the edge of the feeding piece. Preferably, each bore or channel of the feeding piece 41 has its flow path substantially aligned with an outlet 46.

Formation of the microjet and its acceleration are based on the abrupt pressure drop resulting from the steep acceleration undergone by the second fluid 49 on passing through the orifice 46, similarly to the procedure described above for embodiments of FIGS. 1A, 1B and 2 when the second fluid 49 is a gas.

When the second fluid 49 is a gas and the first fluid 48 is a liquid, the microthread formed is quite long and the liquid velocity is much smaller than the gas velocity. In fact, the low viscosity of the gas allows the liquid to flow at a much lower velocity; as a result, the microjet is actually produced and accelerated by stress forces normal to the liquid surface, i.e. pressure forces. Hence, one effective approximation to the phenomenon is to assume that the pressure difference established will result in the same kinetic energy per unit volume for both fluids (liquid and gas), provided gas compressibility effects are neglected. The diameter $d_j$ of the microjet formed from a liquid density $\rho_l$ that passes at a volumetric flow-rate Q through an orifice across which a pressure difference $\Delta P_g$ exists will be given by $$d_j \cong \left(\frac{8\rho_l}{\pi^2 \Delta P_g}\right)^{\frac{1}{4}} Q^{\frac{1}{2}}$$

See Gañàn-Calvo, Physical Review Letters, 80:285–288 (1998).

The relation between the diameter of the microjet, $d_j$, and that of the resulting drops, $\bar{d}$, depends on the ratio between viscous forces and surface tension forces on the liquid on the one hand, and between dynamic forces and surface tension forces on the gas on the other (i.e. on the Ohnesorge and Weber numbers, respectively) (Hinds (*Aerosol Technology*, John & Sons, 1982), Lefevre (*Atomization and Sprays*, Hemisphere Pub. Corp., 1989) and Bayvel & Orzechowski (*Liquid Atomization*, Taylor & Francis, 1993)). At moderate to low gas velocities and low viscosities the relation is roughly identical with that for capillarity instability developed by Rayleigh:

$$\bar{d}=1.89 d_j$$

Because the liquid microjet is very long, at high liquid flow-rates the theoretical rupture point lies in the turbulent zone created by the gas jet, so turbulent fluctuations in the gas destabilize or rupture the liquid microjet in a more or less uneven manner. As a result, the benefits of drop size uniformity are lost.

On the other hand, when the second fluid 49 is a liquid and the first fluid 48 is a gas, the facts that the liquid is much more viscous and that the gas is much less dense virtually equalize the fluid and gas velocities. The gas microthread formed is much shorter; however, because its rupture zone is almost invariably located in a laminar flowing stream, dispersion in the size of the microbubbles formed is almost always small. At a volumetric gas flow-rate $Q_g$ and a liquid overpressure $\Delta P_l$, the diameter of the gas microjet is given by $$d_j \cong \left(\frac{8\rho_l}{\pi^2 \Delta P_l}\right)^{\frac{1}{4}} Q_g^{\frac{1}{2}}$$

The low liquid velocity and the absence of relative velocities between the liquid and gas lead to the Rayleigh relation between the diameters of the microthread and those of the bubbles (i.e. $d=1.89 d_j$).

If both fluids 48, 49 are liquid and scarcely viscous, then their relative velocities will be given by $$\frac{v_A}{v_B} = \left(\frac{\rho_B}{\rho_A}\right)^{\frac{1}{2}}.$$

The diameter of a microjet of the first liquid at a volumetric flow-rate of A $Q_A$ and an overpressure of $B \Delta P_B$ will be given by $$d_j \cong \left(\frac{8\rho_A}{\pi^2 \Delta P_B}\right)^{\frac{1}{4}} Q_A^{\frac{1}{2}}$$

At viscosities such that the velocities of both fluids 48, 49 will rapidly equilibrate in the microjet, the diameter of the microjet of the first liquid will be given by $$d_j \cong \left(\frac{8\rho_B}{\pi^2 \Delta P_B}\right)^{\frac{1}{4}} Q_A^{\frac{1}{2}}$$

The proposed fuel injection nozzle system obviously requires delivery of the fluids 48, 49 to be used in the dispersion process at appropriate flow-rates. Thus:

(1) Both flow-rates should be adjusted for the system so that they lie within the stable parameter window.

(2) The mass ratio between the flows should be compatible with the specifications of each application. Obviously, the gas flow-rate can be increased by using an external means in special applications, since this need not interfere with the aerosolization operation.

(3) If the flow-rates are altered, the characteristic time for the variation should be shorter than the hydrodynamic residence times for the liquid and gas in the microjet, and smaller than the reciprocal of the first natural oscillation frequency of the drop formed at the end of the feeding piece.

(4) Therefore, the gas and liquid can be dispensed by any type of continuous delivery system.

(5) The housing of the pressure chamber and the feeding nozzle can be made from a variety of materials, but preferably materials that are not reactive with organic solutions (e.g. metal or plastic).

Exemplary Uses of the Third Embodiment

FIG. 7 illustrates a generalized, schematic view of an exemplary use of a modified version of the embodiment of FIG. 3 in an injection apparatus. In this figure, the planar feeding element is adapted for use in a cylindrical injection structure. The device provides for either a single cylindrical feeding elements, or more preferably a plurality of concentric cylindrical feeding elements, through which the fuel formulation is introduced for injection. These feeding elements are housed within a single pressure chamber (i.e. one or multiple feeding elements within a single pressure chamber), or each cylindrical feeding element may be housed within multiple chambers, more preferably a single pressure chamber for each feeding element. Alternatively, the feeding elements may be planar, and the device can be comprised from a bank of planar elements that are configured to approximate the desired shape of the nozzle.

Figure 7A:
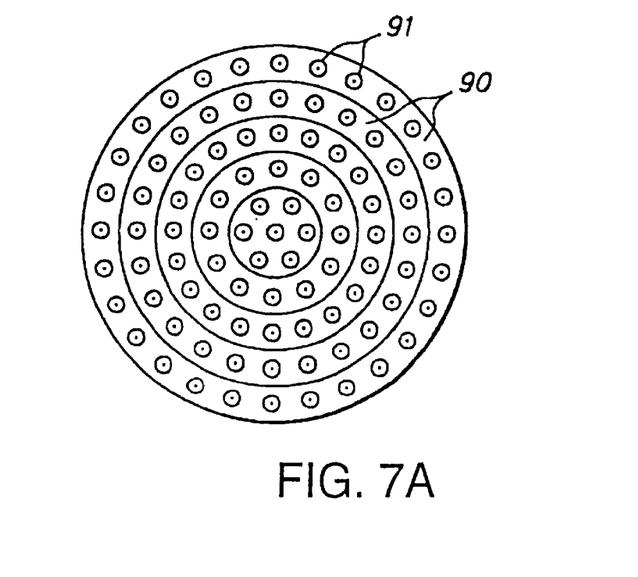
Figure 7B:
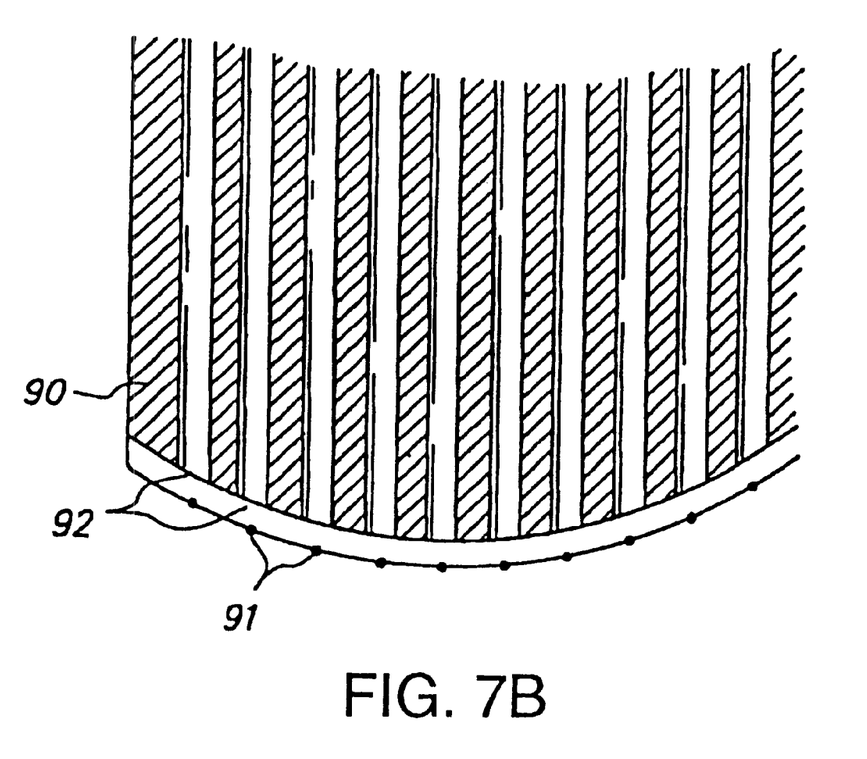

FIG. 7A is a side view of the internal portion of a single, circular feeding element 93 contained within a single pressure chamber 90. The feeding element preferably has multiple recessed chambers within the element 92 to the feeding exit ports 93. The external surface of the exit ports are optionally designed to aid in directing the surrounding gas to the openings in the pressure chamber 91, as is pictured in FIG. 7A. The chambers are aligned with the openings in the pressure chamber to provide better directional flow to the exit openings and to aid in the formation of the focusing tunnel and stable microjet. FIG. 7B illustrates the multiple openings in the pressure chambers of the device containing the same number of multiple, concentric feeding elements and pressure chambers 90.

Fuel Injection Formulation

The compositions used in the invention for producing particles will depend in part on the chemical nature of the formulation to be atomized. For example, if a formulation to be atomized is hydrophobic, e.g. a hydrocarbon, then the solvent containing the formulation used in the method of the invention is preferably a solvent suitable for dissolving hydrophobic compounds, e.g. ether. The hydrophobic components are preferably at least partially dissolved in the solvent. The second fluid is preferably either a gas, more preferably air, or a liquid immiscible with the first.

Fuel formulations for use in the invention may be comprised of any composition that can be aerosolized or atomized for use in an internal combustion reaction delivery. Such formulations preferably contain mixtures of alkanes obtained from petroleum, e.g. natural gas, kerosene, gasoline, diesel fuel and jet fuel. Such formulations, in addition to containing a fuel composition base of molecules such as hydrocarbons, may contain additives that enhance fuel performance and/or reduce harmful emissions, e.g. ethanol. Further examples of fuel compositions may be found in Riegel's Handbook of Industrial Chemistry, ed. J. A. Kent (1992), which is incorporated herein by reference. These formulations may be in any form capable of atomization, such as dissolved in a solvent, suspended in a solvent, or in the form of an emulsion, a slurry, etc., provided the dynamics of the form render it capable of forming a capillary microjet upon exposure to a second fluid.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for producing atomized liquid, comprising the steps of:

forcing a first liquid through a channel of a first feeding source in a manner which causes the first liquid to be expelled from a first exit opening;

forcing a second liquid through a second channel concentrically positioned around the first channel in a manner which causes the second liquid to be expelled from a second exit opening;

forcing a gas through a pressure chamber in a manner which causes the gas to exit the pressure chamber from an exit orifice in front of a flow path of the first and second liquids;

wherein the first liquid and the second liquid are immiscible and the second liquid surrounds the first liquid forming concentric streams which are focused to a stable jet with a stable first liquid-gas interface which flows out of the exit orifice of the pressure chamber; and allowing the stable jet of concentric streams to exit the pressure chamber surrounded by the gas and break up outside the pressure chamber and form spherical coated particles comprised of the first liquid coated with the second liquid.

2. The method of claim 1, wherein the second liquid is kerosene.

3. The method of claim 2, wherein the first liquid is selected from the group consisting of caster oil, ether, and isopropyl nitrate.

4. The method of claim 1, wherein the spherical coated particles have a diameter of about 5 microns to about 500 microns.

5. The method of claim 4, wherein the spherical coated particles have a diameter in a range of from about 10 microns to about 100 microns.

6. The method of claim 1, wherein the second liquid is comprised of a fuel.

7. The method of claim 1, wherein the first liquid is selected from the group consisting of castor oil, ether, and isopropyl nitrate.

8. A fuel injection nozzle comprising:

a first means for providing a first liquid, said means comprising a first fuel entrance port and a first fuel circular exit port having a diameter d;

a second means for providing a second liquid the second means being concentrically positioned about the first means, and comprising a second fuel entrance port and a second fuel exit port wherein the first exit port extends beyond the second exit port by a distance in a range of 0 to 2 d;

a pressure chamber for providing a pressurized gas to an area surrounding the first and second exit ports, the pressure chamber having an exit opening positioned downstream of the first and second exit ports;

wherein the first means for providing the fuel is a feeding needle having a cylindrical channel therein whereby the first fluid entrance port and first fluid exit port are each circular; and wherein the feeding needle exit port has a diameter in the range of from about 0.1 mm to about 2 mm, and the pressure chamber exit port has a diameter in the range of about 0.01 mm to about 2 mm.

9. The nozzle of claim 8, having inserted therein fuel having a dynamic viscosity in the range of from about $10^{-4}$ to about 1 kg/m/sec and wherein the fuel is a hydrocarbon.

10. A fuel injection apparatus comprising the fuel injection nozzle of claim 8.

11. An internal combustion engine comprising the fuel injection apparatus of claim 10.

* * * * *